US00PP15035P3

(12) United States Plant Patent
Olmo

(10) Patent No.: US PP15,035 P2
(45) Date of Patent: Jul. 27, 2004

(54) GRAPEVINE '12-76-71'

(50) Latin Name: *Vitis vinifera*
Varietal Denomination: 12-76-71

(75) Inventor: Harold P. Olmo, Davis, CA (US)

(73) Assignee: Marko Zaninovich, Inc., Delano, CA (US)

( * ) Notice: Subject to any disclaimer, the term of this patent is extended or adjusted under 35 U.S.C. 154(b) by 33 days.

(21) Appl. No.: 09/891,425

(22) Filed: Jun. 27, 2001

(65) Prior Publication Data

US 2003/0014791 P1 Jan. 16, 2003

(51) Int. Cl.[7] ..... A01H 5/00

(52) U.S. Cl. ..... Plt./205

(58) Field of Search ..... Plt./205

(56) References Cited

U.S. PATENT DOCUMENTS

PP12,696 P2 * 6/2002 Karniel ..... Plt./207

* cited by examiner

*Primary Examiner*—Anne Marie Grunberg

(57) ABSTRACT

This new variety '12-76-71' is new and different because of its unusual berry flavor (muscat) combined with bright red coloration and seedless (stenospermic) berries.

3 Drawing Sheets

Genus and species: *Vitis vinifera.*

BACKGROUND AND SUMMARY OF THE INVENTION

The new table grapevine '12-76-71' is of *Vitis vinifera* parentage and resulted from an eighteen year breeding program which had as its goal the development of a grapevine bearing red, seedless, muscat-flavored grapes. The female, seeded parent was the patented grapevine 'Redglobe' (U.S. Plant Pat. No. 4,787). The male parent of the cross was an unnamed, unpatented grapevine designated as grapevine '7-7-2'. Grapevine '7-7-2' bears red, seedless, muscat-flavored berries and descends from a wine grape 'Red Muscatel' and 'Flame Seedless' (both unpatented). The hybridization resulting in grapevine '12-76-71' was made near McFarland, Calif. in 1991. Seeds from this cross were harvested, stratified and planted in a greenhouse. The resulting seedling population totaled 24 individual plants. All seedlings were subsequently transplanted to a field near McFarland, Calif. in March, 1992. Grapevine '12-76-71' fruited in 1993 and was selected for further propagation. It was then propagated by cuttings in McFarland, Calif. and was grafted to 'Freedom' rootstock in 1995 in. This new variety has been found to retain its distinctive characteristics through successive propagation and this novelty is firmed fixed.

The new grapevine variety, grapevine '12-76-71' is similar to its male parent variety '7-7-2', but differs from it by having a much larger berry with firmer flesh. It differs from its female parent 'Redglobe' by having a seedless (stenospermic) berry of much smaller size than that of 'Redglobe'. Fruit cluster size is much smaller than that of 'Redglobe' as well. Harvest time of '12-76-71' is similar to that of its male parent '7-7-2', about two weeks before 'Redglobe' in McFarland, Calif. It differs from other red, seedless varieties such as 'Crimson Seedless' (unpatented) and grapevine '3-14-71' (U.S. Plant Pat. No. 8,297) by ripening about two weeks earlier in the McFarland, Calif. area and by having a strong, muscat flavor.

The accompanying drawings illustrate the following:

DETAILED BOTANICAL DESCRIPTION OF THE INVENTION

Figure 1:
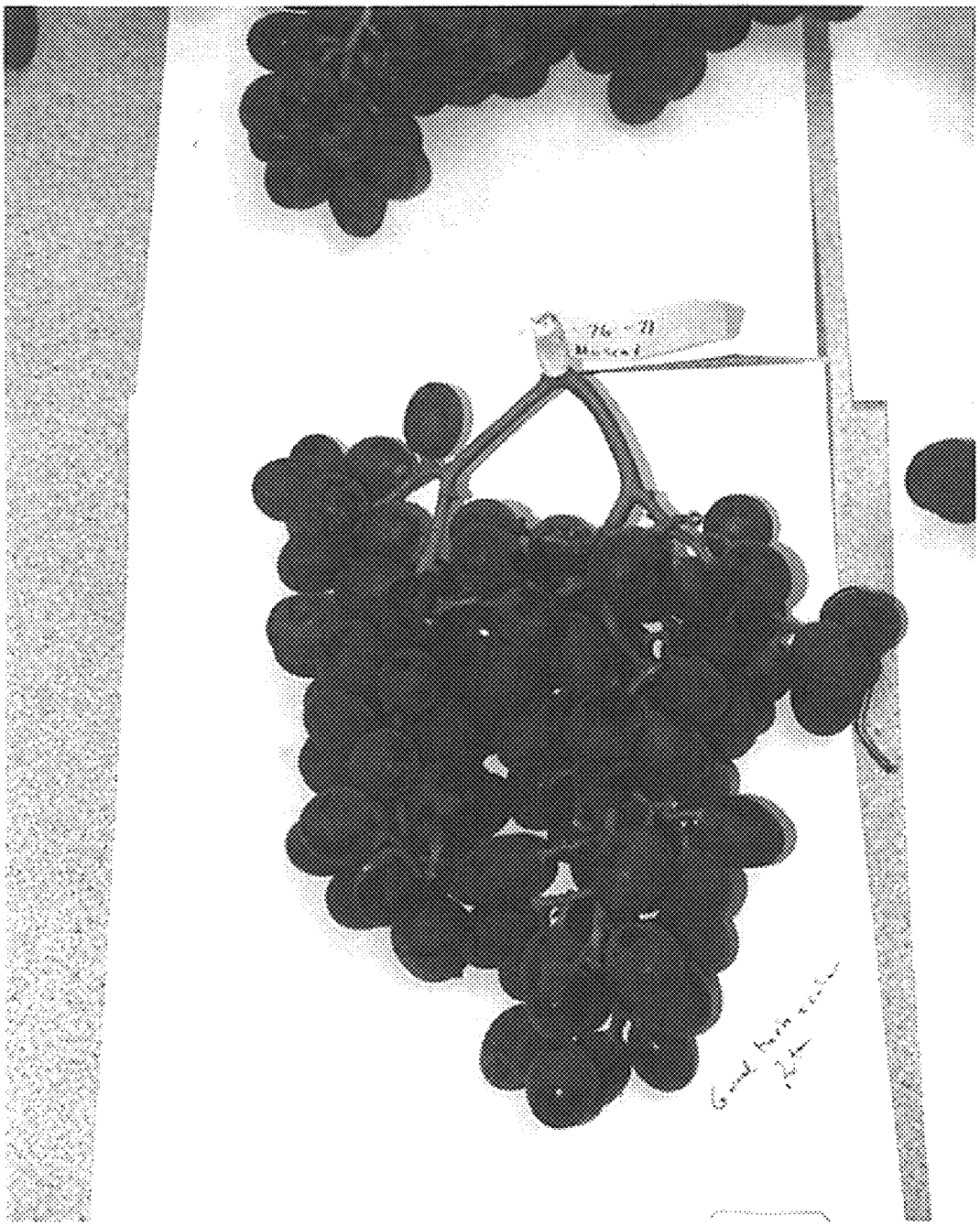
FIG. 1 illustrates the fruit cluster at harvest.
Figure 2:
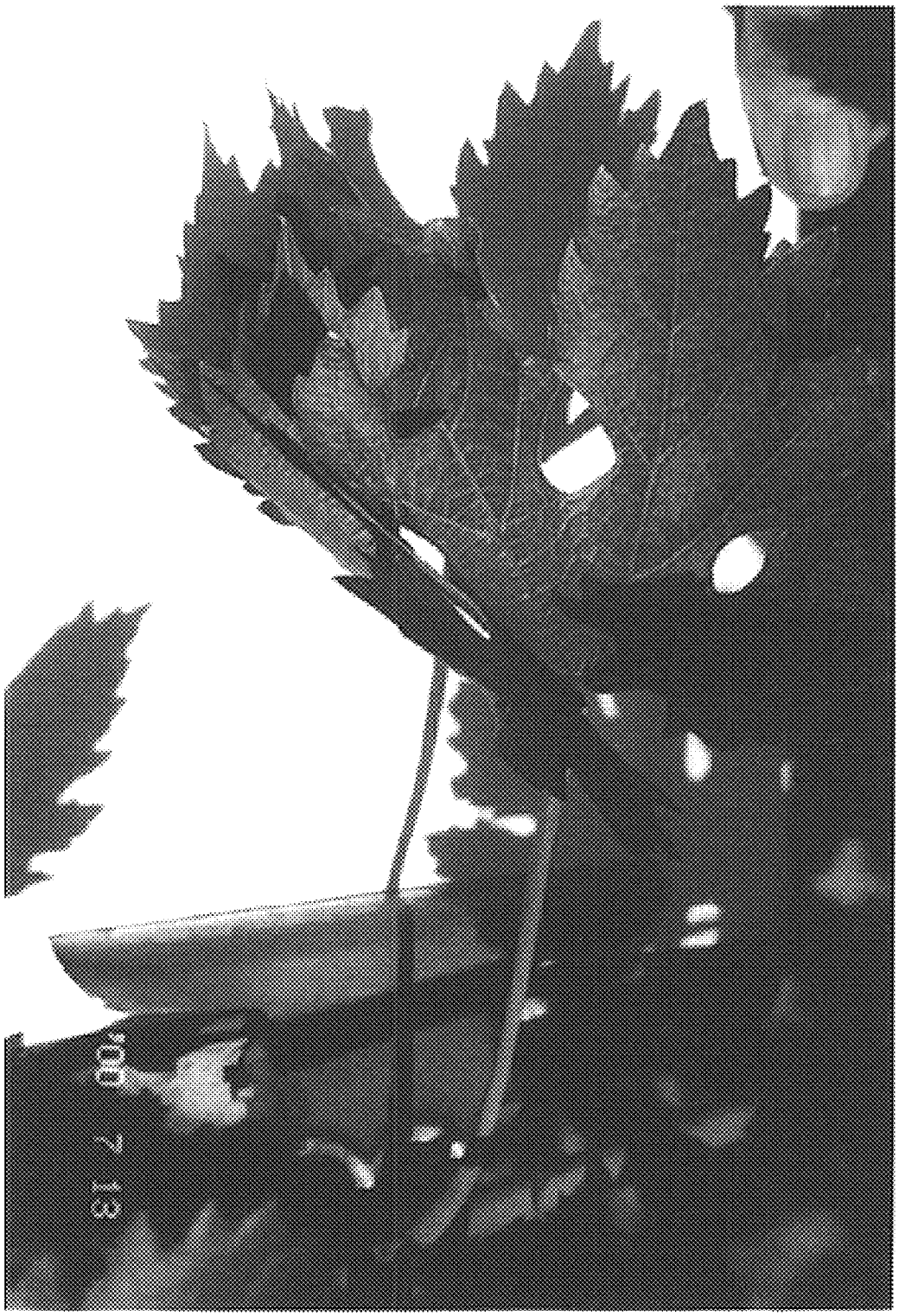
FIG. 2 illustrates the upper leaf surface.
Figure 3:
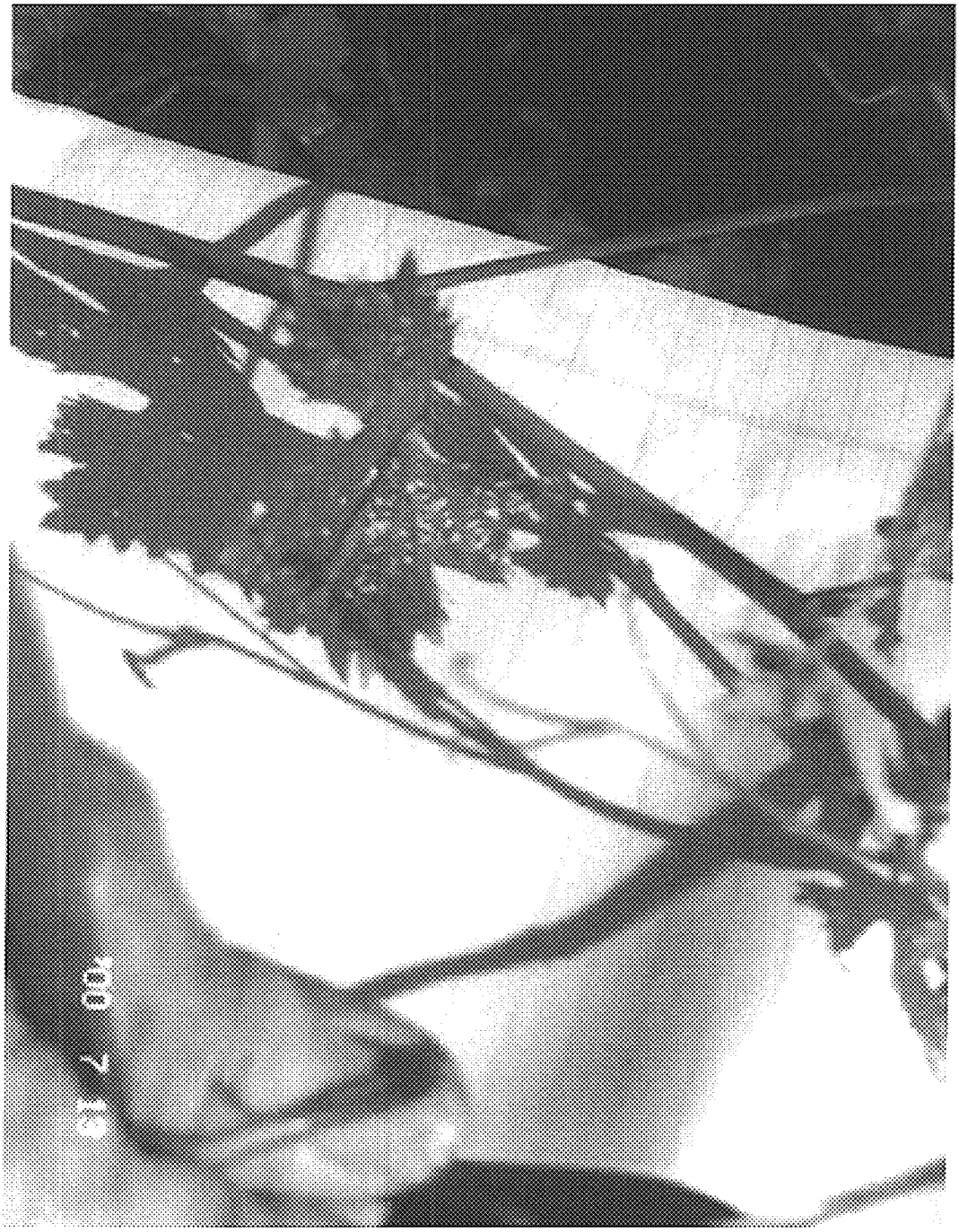
FIG. 3 illustrates the young shoot and leaves.

The following description of grapevine '12-76-71' contains references to color names taken from the Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV).

Descriptions of the new invention apply to vines of '12-76-71' grown on 'Freedom' rootstock at a density of 1,537 vines per hectare grown in Kern County, Calif. in 2000. These vines were in their third year of full production having been planted in 1995. These descriptions are believed to apply generally to the new variety grown under similar circumstances elsewhere:

VINE

General:

*Size.*—5 year old vines on 'Freedom' rootstock are average size — trunk diameter is 55 Millimeters.

*Vigor.*—5 year old vines on 'Freedom' rootstock are average vigor — cane length on vines thinned to 32 shoots averaged 2.25 meters of growth from March-September 2000.

*Density of foliage.*—Moderate.

*Productivity.*—Moderately productive when spur pruned, up to 17,000 kg./hectare.
*Trunk circumference.*—About 6 cm. at 1 meter height.
*Rootstock.*—Freedom.

Trunk:
*Shape.*—Circular.
*Straps.*—Long, split.
*Surface texture.*—Shaggy.
*Inner bark color.*—2.5YR 4/8.

Immature leaves:
*Color.*—10R 4/6 except at margins: 2.5GY 5/6.

Immature shoots:
*Main shoot color* (*shade*).—5GY 5/6.
*Main shoot color* (*sun-exposed*).—5R 4/8.
*Lateral shoot color.*—5GY 5/6.

Mature leaves:
*Adaxial leaf color.*—7.5GY 4/6.
*Abaxial leaf color.*—5GY 5/6.
*Length.*—14.7 cm.
*Width.*—20.1 cm.
*Outline.*—Spherical.
*Leaf margin.*—Cupped upward.
*Lobing.*—5 well-defined lobes.
*Marginal teeth.*—Large.
*Teeth outline.*—Acute.
*Thickness.*—Medium.
*Petoilar sinus.*—Wide, open U-shaped.
*Color of veins, upper surface.*—At apex: 2.5 GY 7/8, at base 5R 3/10.

Shoot tip:
*Color.*—2YR 6/8.
*Pubescence.*—Present.

Petiole:
*Color.*—2.5 GY 7/8 to 5R 4/10.
*Length.*—16.2 cm.

Woody shoot:
*Internode length.*—13.3 cm.
*Cross section.*—Circular.
*Diameter.*—1 cm.
*Shoot surface.*—Rough, ridged.
*Dormant buds.*—Large, flattened.
*Lateral branching.*—Strong.
*Color.*—5YR 5/8.

Flowers:
*Flower sex.*—Perfect.
*Position of first flowering nodes.*—3$^{rd}$.
*Number of inflorescences per shoot.*—1 or 2.
*Number of flowers per inflorescence.*—316.
*Inflorescence branches.*—Slender and irregular in length and Position.
*Date of full bloom.*—May 12, 2000.
*Time of bloom.*—Average compared to other *Vitis vinifera* growing in the McFarland, Calif. area.
*Peduncle length.*—2.8 cm.
*Flower cluster length.*—11.0 cm.
*Pedicel length.*—2 mm.
*Calyptra color.*—2.5GY 7/10.
*Ovary length.*—1.5 mm.
*Ovary width.*—1.5 mm.
*Ovary color.*—2.5GY 6/8.
*Filament length.*—1.5 mm.
*Filament color.*—2.5GY 8/2.
*Anther length.*—0.5 mm.
*Anther color.*—5Y 8/8.

Fruit

General:
*Ripening period.*—About 2 weeks after Flame Seedless near McFarland, Calif.
*Ripening date.*—Jul. 28, 2000.
*Use.*—Fresh market.
*Keeping quality.*—Very good. Clusters stored in early August retained high quality with 94% of berries remaining turgid for a period of 8 weeks at 1 C.
*Disease.*—No disease symptoms have been observed on vines in replicated study in 5 years of growth.
*Insects.*—Grape leafhopper, *Erythroneua elegantula* (Osborn) and variegated leafhhopper, *Erythroneura variabilis* (Beamer) have been observed feeding on vines. No other predaceous insects have been observed.
*Shipping quality.*—Good.
*Date of first harvest.*—Aug. 4, 2000.
*Solids-sugar.*—18 brix.

Cluster:
*Bunch size.*—Small.
*Bunch weight* (*natural*).—170 g.
*Bunch weight* (*gibberellic acid treated*).—375 g.
*Form.*—Mostly conical, but irregular.

Berry:
*Size.*—Medium.
*Uniformity of size.*—Uniform.
*Berry weight* (*natural*).—2.3 g.
*Berry weight* (*gibberellic acid treated*).—4–8 g, 5.4 g average.
*Shape.*—Spherical.
*Berry length* (*natural*).—1.8 cm.
*Berry diameter* (*natural*).—1.6 cm.
*Berry length with gibberellic acid application.*—2.5 cm.
*Berry diameter with gibberellic acid application.*—2.2 cm.
*Presence of seeds.*—Rudimentary.
*Cross section.*—Circular.
*Skin color.*—5R 4/6.
*Juiciness of flesh.*—Very juicy.
*Flesh color.*—5GY 7/4.
*Rudimentary seed color.*—5GY 7/8.
*Berry firmness.*—Very firm.
*Particular flavor.*—Muscat, strong.
*Bloom.*—Strong.
*Berry separation from pedicel.*—Requiring great force; exceptional attachment.

Skin:
*Thickness.*—Medium.
*Texture.*—Smooth.
*Reticulation.*—Absent.
*Tenacity.*—Tenacious to flesh.
*Tendency to crack.*—Resistant.

Tendrils:
*Conformation.*—Bifurcated or trifurcated.
*Color.*—5GY 7/8.
*Length.*—24.4 cm.

What is claimed is:

1. A new and distinct variety of grapevine plant, substantially as illustrated and described.

* * * * *